(12) United States Patent
Shankar et al.

(10) Patent No.: US 9,187,409 B2
(45) Date of Patent: Nov. 17, 2015

(54) SYNTHESIS OF ALISKIREN

(75) Inventors: Rama Shankar, Hyderabad (IN); Vadali Lakshmana Rao, Hyderabad (IN); Palla Vijay Kumar, Hyderabad (IN); Saidugari Swamy, Hyderabad (IN); Dasari Srinivasa Rao, Hyderabad (IN); Srinivasa Rao Potla, Hyderabad (IN); Mittapelly Nagaraju, Hyderabad (IN); Jaldu Ravikanth, Hyderabad (IN); Vijaya Krishna Ravi, Hyderabad (IN); Seshadri Rao Manukonda, Hyderabad (IN); Dandala Ramesh, Hyderabad (IN)

(73) Assignee: Mylan Laboratories Limited, Hyderabad (IN)

(*) Notice: Subject to any disclaimer, the term of this patent is extended or adjusted under 35 U.S.C. 154(b) by 4 days.

(21) Appl. No.: 13/879,849

(22) PCT Filed: Oct. 19, 2011

(86) PCT No.: PCT/IB2011/002507
§ 371 (c)(1),
(2), (4) Date: Jun. 4, 2013

(87) PCT Pub. No.: WO2012/052829
PCT Pub. Date: Apr. 26, 2012

(65) Prior Publication Data
US 2013/0261324 A1    Oct. 3, 2013

(30) Foreign Application Priority Data

Oct. 19, 2010  (IN) .......................... 3087/CHE/2010
Jul. 13, 2011  (IN) .......................... 2395/CHE/2011

(51) Int. Cl.
| | | |
|---|---|---|
| C07C 231/12 | (2006.01) |
| C07C 237/22 | (2006.01) |
| C07C 233/00 | (2006.01) |
| C07C 43/205 | (2006.01) |
| C07C 231/14 | (2006.01) |
| C07C 43/215 | (2006.01) |
| C07C 241/00 | (2006.01) |
| C07C 255/29 | (2006.01) |
| C07C 247/10 | (2006.01) |
| C07D 307/33 | (2006.01) |

(52) U.S. Cl.
CPC ............. *C07C 231/14* (2013.01); *C07C 43/215* (2013.01); *C07C 231/12* (2013.01); *C07C 241/00* (2013.01); *C07C 247/10* (2013.01); *C07C 255/29* (2013.01); *C07D 307/33* (2013.01)

(58) Field of Classification Search
CPC .. C07C 255/29; C07C 43/215; C07C 231/12; C07D 307/33
USPC .......................... 564/124, 158, 163; 568/608
See application file for complete search history.

(56) References Cited

U.S. PATENT DOCUMENTS

| | | |
|---|---|---|
| 5,559,111 A | 9/1996 | Goschke et al. |
| 6,730,798 B2 | 5/2004 | Stutz et al. |
| 6,800,769 B2 | 10/2004 | Stutz et al. |
| 7,009,078 B1 | 3/2006 | Herold et al. |
| 7,132,569 B2 | 11/2006 | Herold et al. |

OTHER PUBLICATIONS

Sandham, D A et al. "A Convergent Synthesis of the Renin Inhibitor CGP05368," Tetrahedron Letters, Elsevier, Amsterdam, 2000.

*Primary Examiner* — Barbara P Badio

(57) ABSTRACT

The present invention provides novel process for the preparation of renin inhibitor Aliskiren or its derivatives, and its pharmaceutically acceptable salts. The present invention also provides novel intermediates used in the preparation of Aliskiren.

10 Claims, No Drawings

SYNTHESIS OF ALISKIREN

FIELD OF THE INVENTION

The present invention relates to novel process for the preparation of renin inhibitor Aliskiren or its derivatives, and its pharmaceutically acceptable salts.

BACKGROUND OF THE INVENTION

Aliskiren, (2S,4S,5S,7S)—N-(2-carbamoyl-2-methylpropyl)-5-amino-4-hydroxy-2,7-diisopropyl-8-[4-methoxy-3-(3-methoxypropoxy)phenyl]octanamide having the Formula-I, a new antihypertensive has been developed which interferes with the renin-angiotensin system at the beginning of angiotensin II biosynthesis.

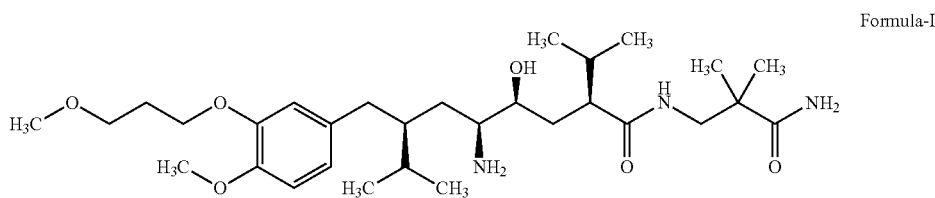 [SMILES: COCCCOc1cc(C[C@@H](C[C@H](N)[C@@H](O)C[C@H](C(=O)NCC(C)(C)C(N)=O)C(C)C)C(C)C)ccc1OC]

Formula-I

Aliskiren is marketed by Novartis as TEKTURNA® in the form of its hemifumarate salt in a once-daily formulation. More recently Aliskiren is also formulated as combination with other API.

U.S. Pat. No. 5,559,111 discloses Aliskiren and related compounds along with the different approaches for the synthesis of Aliskiren.

Further U.S. Pat. No. 7,132,569, U.S. Pat. No. 7,009,078, U.S. Pat. No. 6,730,798 and U.S. Pat. No. 6,800,769 claims novel intermediates used in the preparation of Aliskiren and process for the preparation of Aliskiren, which are incorporated here for reference.

As the compound comprises, 4 chiral carbon atoms, the synthesis of the enantiomerically pure compound is quite demanding. Therefore, novel routes of synthesis needed for the preparation of Aliskiren.

The present invention provides novel intermediates used in the preparation of Aliskiren and process for the preparation of Aliskiren.

OBJECT AND SUMMARY OF THE INVENTION

Principle object of the present invention is to provide a novel process for the preparation of Aliskiren, (2S,4S,5S,7S)—N-(2-carbamoyl-2-methylpropyl)-5-amino-4-hydroxy-2,7-diisopropyl-8-[4-methoxy-3-(3-methoxypropoxy)phenyl]octanamide or its pharmaceutically acceptable salts.

Another object of the present invention is to provide novel intermediate of compound of Formula-III used in the preparation of Aliskiren.

In one aspect the present invention provides, novel process for the preparation of renin inhibitor of compound of Formula-Ia comprising the steps of:

a) reacting compound of Formula-II, with a cyano compound 3-Amino-2,2-dimethyl-propionitrile

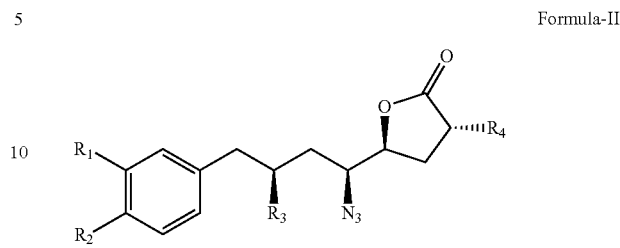

Formula-II wherein $R_1$ and $R_2$ are independently of one another H, $C_1$-$C_6$ alkyl, $C_1$-$C_6$ halogen alkyl, $C_1$-$C_6$alkoxy, $C_1$-$C_6$alkoxy-$C_1$-$C_6$alkyl, or $C_1$-$C_6$ alkoxy-$C_1$-$C_6$alkyloxy, $R_3$ is $C_1$-$C_6$ alkyl, $R_4$ is $C_1$-$C_6$alkyl, to form a compound of Formula-III,

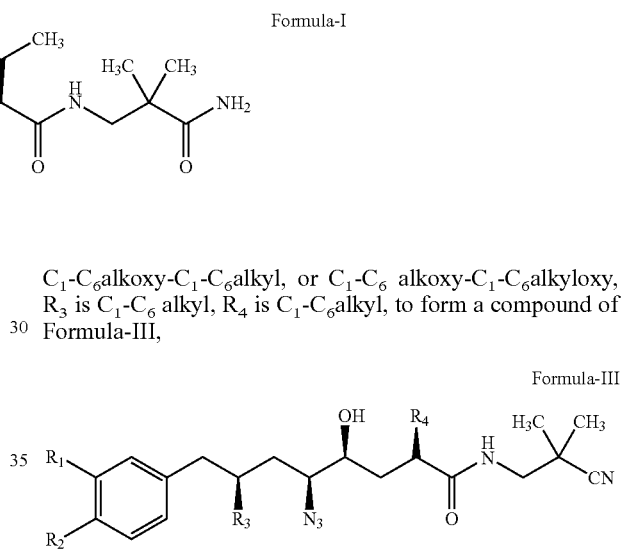

Formula-III b) converting cyano group of compound of Formula-III into amide group to give compound of Formula-IV Formula-IV

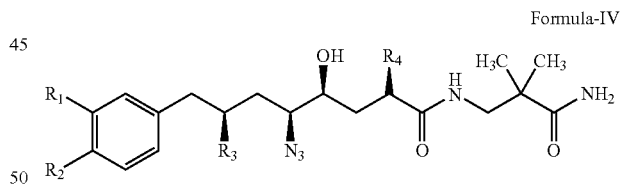

c) reducing azide group of compound of Formula-IV to form the amine group and isolating the compound of Formula-Ia; and Formula-Ia

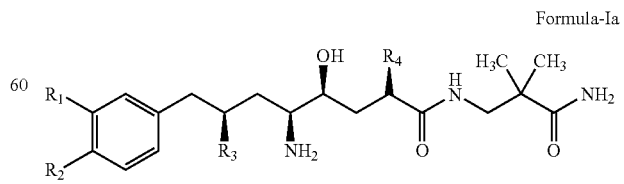

d) optionally converting compound of Formula-Ia into pharmaceutically acceptable salts.

DETAILED DESCRIPTION OF THE INVENTION

The present invention relates to novel process for the preparation of renin inhibitors like Aliskiren or its pharmaceutically acceptable salts.

The present invention further relates to novel intermediates used in the preparation of Aliskiren or its pharmaceutically acceptable salts.

The main aspect of the present invention provides, novel process for the preparation of renin inhibitor of compound of Formula-Ia comprising the steps of:

a) reacting compound of Formula-II, with a cyano compound 3-Amino-2,2-dimethyl-propionitrile

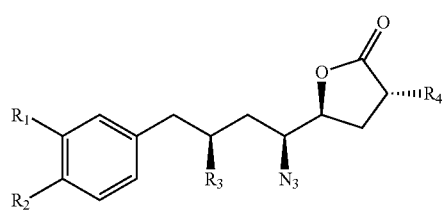

Formula-II wherein $R_1$ and $R_2$ are independently of one another H, $C_1$-$C_6$ alkyl, $C_1$-$C_6$ halogen alkyl, $C_1$-$C_6$ alkoxy, $C_1$-$C_6$ alkoxy-$C_1$-$C_6$ alkyl, or $C_1$-$C_6$ alkoxy-$C_1$-$C_6$ alkyloxy, $R_3$ is $C_1$-$C_6$ alkyl, $R_4$ is $C_1$-$C_6$ alkyl, to form a compound of Formula-III,

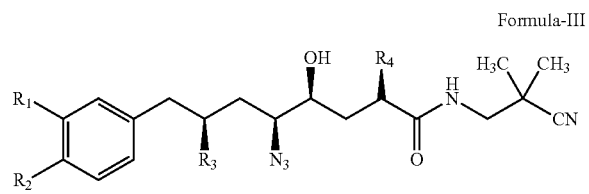

Formula-III b) converting cyano group of compound of Formula-III into amide group to give compound of Formula-IV;

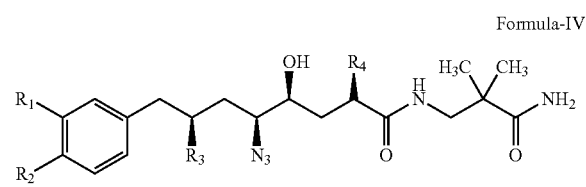

Formula-IV c) reducing azide group of compound of Formula-IV to form the amine group and isolating the compound of Formula-Ia; and

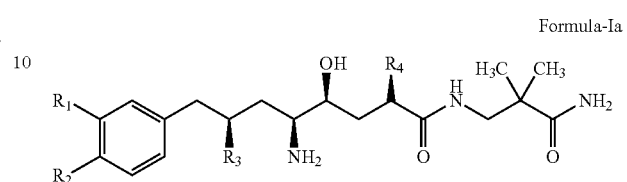

Formula-Ia d) optionally converting compound of Formula-Ia into pharmaceutically acceptable salts.

In one embodiment, the obtained renin inhibitor compound of Formula-Ia is Aliskiren of Formula-I, wherein $R_1$ is $O(CH_2)_3OCH_3$, $R_2$ is $OCH_3$, $R_3$ and $R_4$ are isopropyl groups.

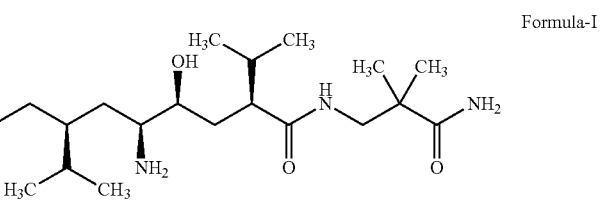

Formula-I

In literature Aliskiren has been prepared by aminolysis of the lactone intermediate with an amine followed by the reduction to get the 5,4-amino alcohol moiety. The aminolysis of the lactone has been carried out with 3-amino-2,2-dimethyl-propionamide. It has been disclosed in literature that this aminolysis reaction is best carried out in neat with out a solvent using excess of 3-amino-2,2-dimethylpropionamide. It has been suggested that this aminolysis reaction could be only completed if the amide used 5 mol equivalents with respect to lactone. Also it has been described that the aminolysis can be completed in reasonable time if the reaction is carried out at higher temperature about 90-100° C. It is described in literature that this aminolysis reaction is a reversible reaction and the reaction equilibrium can be only shifted to right if more quantity of the amine is used. Therefore to have a industrially/commercially viable process for production of aliskiren its imperative to have a reaction condition where this aminolysis could be done in reasonable time at comparatively lower temperature along with a simple recovery process for the un reacted 3-amino-2,2-dimethylpropionamide. The 3-amino-2,2-dimethyl-propionitrile being a liquid at room temperature in contrast to the 3-amino-2,2-dimethylpropionamide which is a solid using 3-amino-2,2-dimethyl-propionitrile for the aminolysis reaction in neat condition give a uniform homogeneous reaction mass causing effective mixing of the two reactants and thus a better, faster reaction. Also 3-amino-2,2-dimethyl-propionitrile being a liquid having lower solubility in water compare to the 3-amino-2,2-dimethylpropionamide its recovery after reaction form the reaction system by acid base treatment is much easier and effective. There by resulting almost quantitative recovery of unreacted/unused 3-amino-2,2-dimethyl-propionitrile. Further the 3-amino-2,2-dimethyl-propionitrile having lower boiling point it is easy to purify by distillation either during its preparation/recovery.

Accordingly compound of Formula-III is prepared by the reaction of compound of Formula-II with 3-Amino-2,2-dimethyl-propionitrile optionally in the presence of a base. The base used in this step may be organic or inorganic base, preferably organic base such as Triethylamine, diisopropylethylamine, etc., more preferably Triethylamine.

In one more embodiment cyano group of compound of Formula-III is converted into amide group in the presence of a base and an oxidizing agent like hydrogen peroxide. The base used here may be organic or inorganic base, preferably inorganic base such as alkaline earth metal hydroxides, carbonates, bicarbonates etc., more preferably Sodium hydroxide.

The amide compound of Formula-IV is converted into Aliskiren of compound of Formula-I by reducing the compound of Formula-IV. The process comprises reducing the azide group of compound of Formula-IV in the presence of alcoholic solvents and isolating Aliskiren or its pharmaceutically acceptable salts.

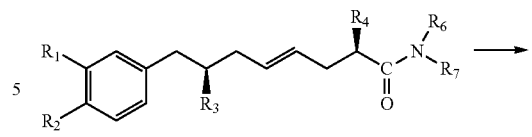

Formula-V

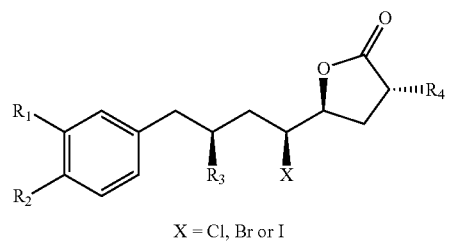

X = Cl, Br or I

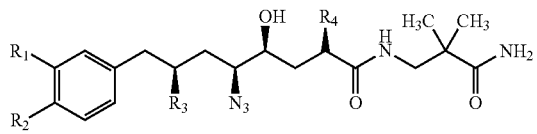

Formula-IV

Pd/C
Alcohol solvents

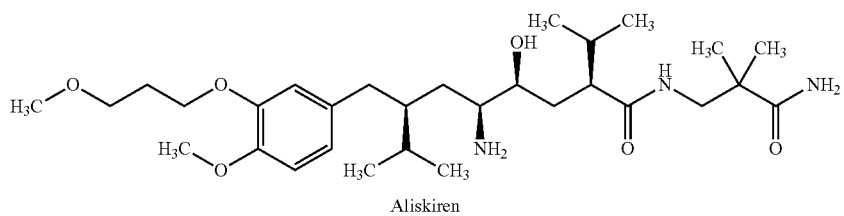

Aliskiren

In one embodiment, the reduction of compound of Formula-IV is carried out in the presence of Palladium catalyst.

In one more embodiment, alcoholic solvents used in the reduction of azide intermediate is selected from ethanol, methanol and isopropanol, preferably methanol and ethanol.

The prior art processes involves the use of tert-butyl methyl ether as a solvent in the reduction of azide intermediate. The yield obtained by this process is low.

In one more embodiment the lactone compound of Formula-II is prepared by the conventional prior art methods for example disclosed in U.S. Pat. No. 7,009,078.

The compound of Formula-II is alternatively prepared by cyclisation and azidation of the compound of Formula-V. The process for the preparation of compound of Formula-II from compound of Formula-V is schematically shown below.

-continued

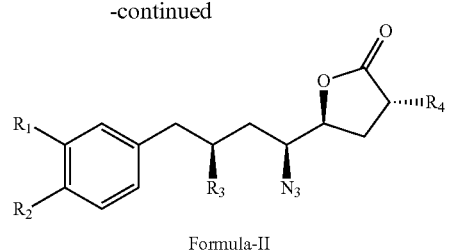

Formula-II

The compound of Formula-V, wherein $R_1$, $R_2$, $R_3$ and $R_4$ are defined above, $R_6$ is $C_1$-$C_6$ alkyl, $R_7$ is $C_1$-$C_6$ alkyl or C1-$C_6$ alkoxy, including the preferences, Y is Cl, Br or I, and Z is Cl, Br or I is prepared by condensing the compound of Formula-A with Compound of Formula-B in the presence of an alkali metal or alkaline earth metal, wherein the improvement comprises after completion of the reaction the formed compound of Formula-V is purified by fractional distillation.

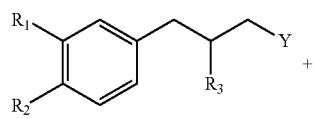

Compound-A

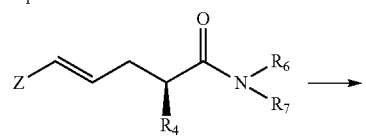

Compound-B

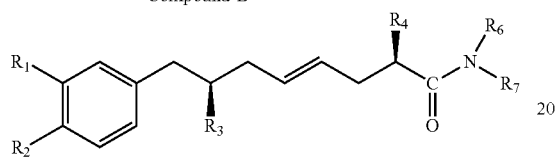

Formula-V wherein $R_1$, $R_2$, $R_3$ and $R_4$ are defined above, $R_6$ is $C_1$-$C_6$ alkyl, $R_7$ is $C_1$-$C_6$ alkyl or $C_1$-$C_6$ alkoxy, including the preferences, Y is Cl, Br or I, and Z is Cl, Br or I.

Prior art U.S. Pat. No. 7,132,569 discloses that the compound of Formula-V is purified by using flash chromatography, which is not suitable on commercial scale. Present invention provides purification of compound of formula V by using fractional distillation method.

The condensation of compound of Formula-A and compound of Formula-B takes place in the presence of alkali or alkaline earth metals like magnesium. The coupling of Grignard reagents with compound of formula B in an ether such as, for example, tetrahydrofuran, methyl tetrahydrofuran or dioxan as solvents in the presence of catalytic quantities of a soluble metal complex, for example an iron complex such as iron acetonyl acetate, and in the presence of more than equimolar quantities of a solvent stabilizing the metal complex, for example N-methylpyrrolidone. It is expedient to carry out the reaction so that initially a compound of formula-A is converted to a Grignard compound (for example with magnesium) and then adding a solution of a compound of formula-B, metal complex and N-methylpyrrolidone, or vice versa.

According to the present invention, fraction-I, which contains low boiling impurities are distilled out at bath/mass temperature of 90° C. to 150° C., (vapour temperature 40° C. to 130° C.), preferably at a temperature of 110° C. to 130° C., (vapour temperature 60° C. to 110° C.). Fraction-II, which contains starting material A2, Methyl impurity and hydroxyl impurities are distilled out at bath/mass temperature of 170° C. to 260° C., (vapour temperature 120° C. to 180° C.), preferably at a temperature of 200° C. to 240° C., (vapour temperature 140° C. to 160° C.) to yield the compound of Formula-V. The purity of the compound increases from 70 to above 90% after distillation; preferably it is above 95%. This purity will enhance the purity of Aliskiren.

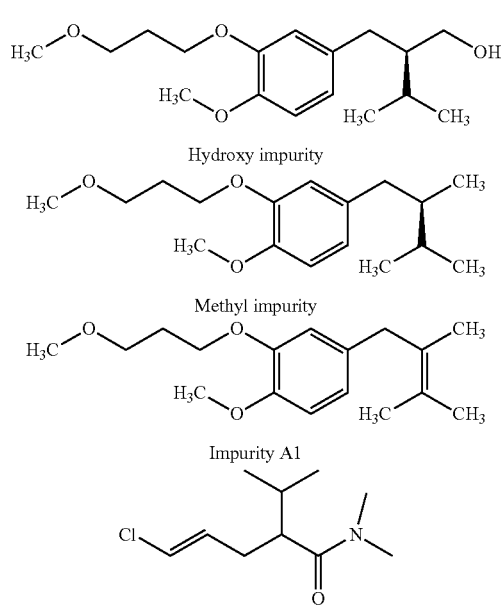

The compounds of Formula-A and Formula-B are prepared as per the conventional methods, for example the processes disclosed in U.S. Pat. No. 5,559,111 and U.S. Pat. No. 7,009,078.

Process for the preparation of Aliskiren as per the present invention, is summarized in the scheme-I.

Scheme-1

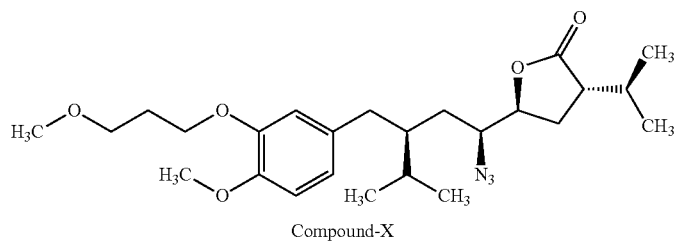

Compound-X

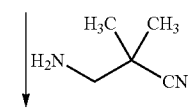

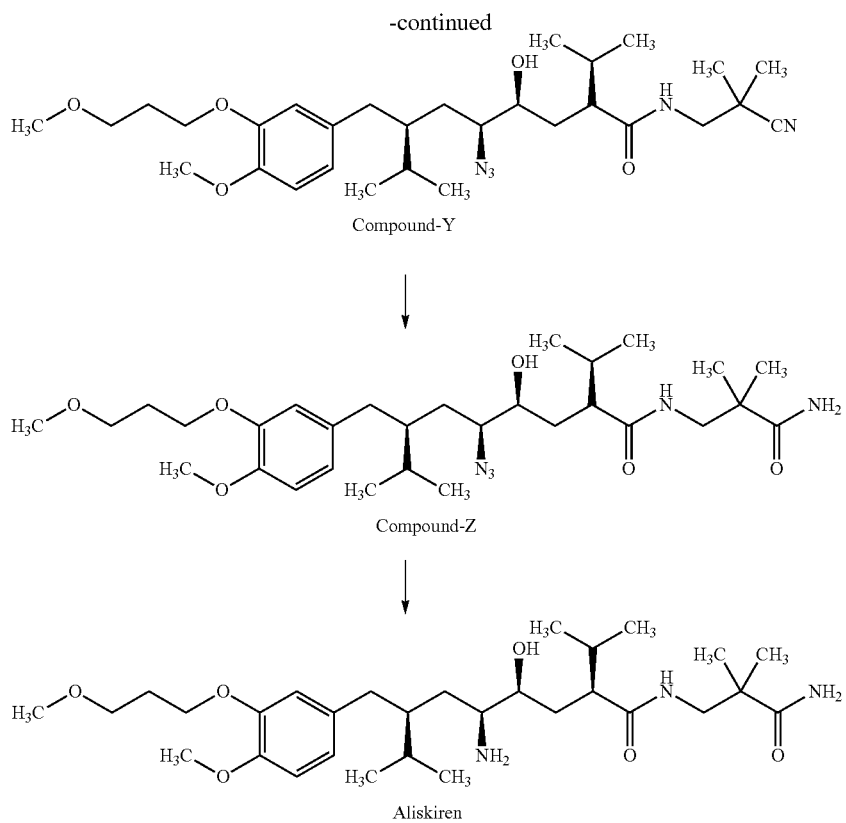

Compound-Y

Compound-Z

Aliskiren

In one more aspect, the present invention provides novel intermediate of compound of Formula-III Formula-III

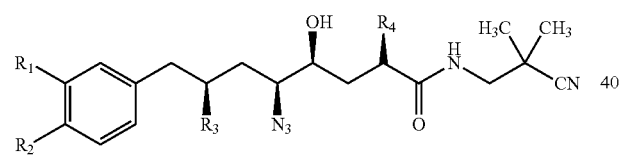

wherein $R_1$ and $R_2$ are independently of one another H, $C_1$-$C_6$ alkyl, $C_1$-$C_6$ halogen alkyl, $C_1$-$C_6$alkoxy, $C_1$-$C_6$alkoxy-$C_1$-$C_6$alkyl, or $C_1$-$C_6$ alkoxy-$C_1$-$C_6$alkyloxy, $R_3$ is $C_1$-$C_6$ alkyl, and $R_4$ is $C_1$-$C_6$ alkyl.

In one embodiment, the compound of Formula-III is converted into Aliskiren or its pharmaceutically acceptable salts thereof.

The following examples are provided to illustrate the process of the present invention. They, are however, not intended to limiting the scope of the present invention in any way and several variants of these examples would be evident to person ordinarily skilled in the art.

EXPERIMENTAL PROCEDURE

Example-1

Synthesis of 3-Amino-2,2-dimethyl-propionitrile

A mixture of 3-amino-2,2-dimethylpropionamide (2.0 g) and thionyl chloride (3.0 g) in 15 ml ethylenedichloride was refluxed at 75-80° C. for a period of 5 hrs. The reaction mixture was concentrated to remove excess thionyl chloride and the residue was diluted with dichloromethane and washed with saturated sodium hydrogen carbonate solution. The dichloromethane solution was further washed with brine and concentrated to get 3-Amino-2,2-dimethyl-propionitrile as an oil.

Example-2

Synthesis of 3-Amino-2,2-dimethyl-propionitrile

A mixture of 3-amino-2,2-dimethylpropionamide (10 g) and $POCl_3$ (40 g) in 50 ml toluene was maintained at 90-95° C. for a period of 12-16 hrs. The reaction mixture was concentrated to remove excess $POCl_3$. The reaction mass was cooled to 10-15° C. and diluted with water. pH of the reaction mass was adjusted 14 with 30% aq. Sodium hydroxide solution. The aqueous layer was extracted with dichloromethane (2×50 mL). Combined dichloromethane layer was washed with brine solution (20 mL) and concentrated to get 3-Amino-2,2-dimethyl-propionitrile (7 g) as an oil.

Example-3

Process for the Preparation of Compound of Formula-V (where $R_1$=$OCH_2OCH_2CH_3$, $R2$=$OCH_3$, $R_3$, $R_4$=—$CH(CH_3)_2$, and $R_6$, $R_7$=Me)

A mixture of magnesium powder (15.5 g) and 2-methyltetrahydrofuran (175 ml) was heated to 60° C. and 1,2-dibromoethane (1 ml) was added over a period of 2 minutes. A solution of 2-{4-methoxy-3-(3-methoxypropoxyl)]-phenyl-methyl-3-methyl-1-chlorobutane (50 g), 1,2-dibromoethane (5.6 ml) and 2-methyltetrahydrofuran (500 ml) was added dropwise over a period of 15 minutes at 60-65° C. The reaction mixture was stirred under reflux and cooled to ambient temperature. There after was added to a solution of 5-chloro-2-isopropyl-n,n-dimethylpent-4-enamide-(2S,4E) (27.5 g), N-methylpyrrolidone (0.30 g) and iron (III) acetyl acetonate (1.2 g) in 2-methyltetrahydrofuran (300 ml). The reaction mixture was agitated further 15 minutes at 10° C. and quenched with dilute hydrochloric acid. The reaction mixture was extracted with ethyl acetate and the organic phases washed consecutively with water and saturated aqueous sodium chloride solution. The combined organic phases were dried over sodium sulfate, filtered and concentrated. Product purified by fractional distillation (0.1-3 mbar) at 250° C. The unreacted starting materials along with the process byproducts are removed at 200° C. under reduced pressure leaving behind pure product. (~57 g, 80% yield).

Example-4

Process for the Preparation of Compound of Formula-V (where $R_1$=OCH$_2$OCH$_2$CH$_3$, R2=OCH$_3$, $R_3$, $R_4$=—CH(CH$_3$)$_2$, and $R_6$, $R_7$=Me)

A mixture of Magnesium powder (15.5 g) and tetrahydrofuran (175 ml) was heated to reflux and 1,2-dibromoethane (1 ml) was added over a period of 2 minutes. A solution of 2-{4-methoxy-3-(3-methoxypropoxyl)]-phenylmethyl-3-methyl-1-chlorobutane (50 g), 1,2-dibromoethane (5.6 ml) and Tetrahydrofuran (500 ml) was added dropwise over a period of 15 minutes at 60-65° C. The reaction mixture was stirred under reflux and cooled to ambient temperature. There after was added to a solution of 5-chloro-2-isopropyl-n,n-dimethylpent-4-enamide-(2S,4E) (27.5 g), N-methylpyrrolidone (0.30 g) and iron (III) acetyl acetonate (1.2 g) in tetrahydrofuran (300 ml). The reaction mixture was agitated further 15 minutes at 10° C. and quenched with dilute hydrochloric acid. The reaction mixture was extracted with diisopropylether and the organic phases washed consecutively with water and saturated aqueous sodium chloride solution. The combined organic phases were dried over sodium sulfate, filtered and concentrated. Product purified by fractional distillation (0.1-3 mbar) at 250° C. The unreacted starting materials along with the process byproducts are removed at 200° C. under reduced pressure leaving behind pure product. (~57 g, 80% yield).

Example-5

Process for the Preparation of Compound of Formula-V (where $R_1$=OCH$_2$OCH$_2$CH$_3$, R2=OCH$_3$, $R_3$, $R_4$=—CH(CH$_3$)$_2$, and $R_6$, $R_7$=Me)

A mixture of magnesium powder (8.4 g) and tetrahydrofuran (75 ml) was heated to 60-65° C. and Iodine (100 mg) was added. A solution of 2-{4-methoxy-3-(3-methoxypropoxyl)]-phenylmethyl-3-methyl-1-chlorobutane (40 g), 1,2-dibromoethane (1.2 g) and tetrahydrofuran (200 ml) was added dropwise over a period of 15-30 minutes at 60-65° C. The reaction mixture was stirred under reflux and cooled to ambient temperature. There after was added a solution of 5-chloro-2-isopropyl-n,n-dimethylpent-4-enamide-(2S,4E) (25.4 g), N-methylpyrrolidone (0.36 g) and iron (III) acetyl acetonate (0.54 g) in tetrahydrofuran (300 ml) at 0° C. The reaction mixture was agitated further 15 minutes at 10° C. and quenched with dilute hydrochloric acid. The reaction mixture was extracted with diisopropylether and the organic phases washed consecutively with water and saturated aqueous sodium chloride solution. The combined organic phases were dried over sodium sulfate, filtered and concentrated. Product purified by fractional distillation (0.1-3 mbar) at 250° C. The unreacted starting materials along with the process byproducts are removed at 200° C. under reduced pressure leaving behind pure product. (~46 g, 80% yield).

Example-6

Preparation of Bromo Lactone Compound

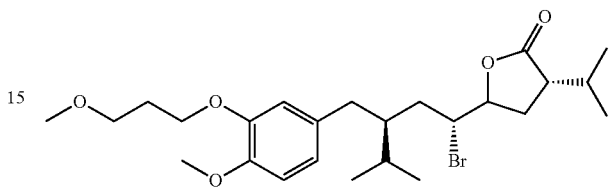

Compound of Formula-V (15 gm), obtained from example-2 and THF (165 ml) was taken in a RB flask at 30° C. To this reaction mixture DM water (1.68 ml) was added and stirred. The reaction mass was cooled and to this orthophosphoric acid (2.3 ml) and N-bromo succinamide (6.6 gm) were added lotwise alternatively in every 3 min gap and temperature was maintained at 5° C. for 1-2 hrs. After completion of the reaction, reaction mass was quenched with Sodium hydrogen sulphite and reaction mass was extracted with isopropyl ether (225 ml). Organic layer was washed with 1N HCl (150 ml) followed by water. The organic layer was washed with saturated sodium bicarbonate solution and brine solution. Organic layer was dried with sodium sulphate and the solvent was distilled out completely under vacuum. The obtained residue was crystallized in a mixture of 1:2 IPE/n-hexane. The compound was filtered and washed with pre cooled 1:2 IPE/n-hexane. The wet compound was dried to yield Bromo lactone compound.

Example-7

Process for the Preparation of Azide Compound-X

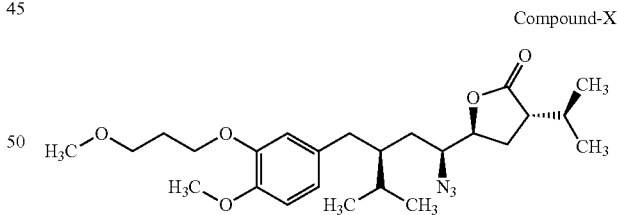

Compound-X

Toluene (150 ml) and the bromo lactone compound (4.28 gm) obtained from example-3 was taken in a flask and sodium azide (5.2 gm) was added. To this DM water (10 ml) and Aiquat-336 (1.0 gm) was added and the reaction mass was maintained at 75-80° C. for 48 hrs. To this DM water (50 ml) was added. The layers were separated and reaction mass was extracted with toluene (100 ml). Organic layers were combined and washed with DM water (50 ml). Organic layer was dried with sodium sulphate and the solvent was distilled out completely under vacuum. The Obtained residue, was crystallized in a mixture of 1:2 IPE/n-hexane. The compound was filtered and washed with pre cooled 1:2 IPE/n-hexane. The wet compound was dried to yield azide compound-X.

Example-8

Synthesis of Compound-Y

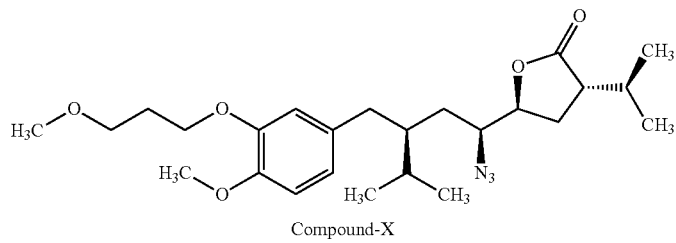
Compound-X

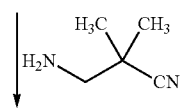

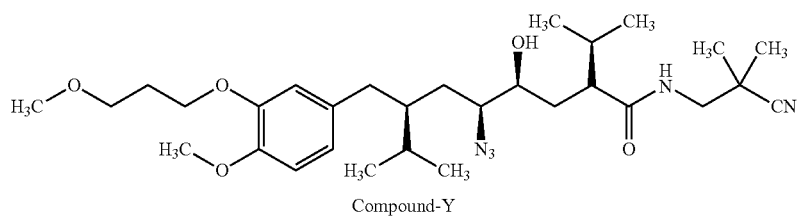
Compound-Y

A mixture of compound-X (12.0 g), 3-Amino-2,2-dimethyl-propionitrile (4.2 g), 45 mg 2-hydroxypyridine in 12 ml triethylamine was stirred for about 30 hours at 80-90° C. The progress of the reaction was monitored by HPLC analysis. After completion of the reaction it was concentrated to residue and the residue was dissolved in diisopropyl ether and stirred with aqueous NaOH to remove unreacted compound X. The layers were separated and the diisopropyl ether extract was concentrated to give residue (13.0 g).

Example-9

Synthesis of Compound-Y

A mixture of compound-X (12.0 g), 3-Amino-2,2-dimethyl-propionitrile (4.2 g), 3.7 g of 2-hydroxypyridine in 12 ml triethylamine was stirred for about 30 hours at 80-90° C. The progress of the reaction was monitored by HPLC analysis. After completion of the reaction it was concentrated to residue and the residue was dissolved in diisopropyl ether and stirred with aqueous NaOH to remove unreacted compound X. The layers were separated and the diisopropyl ether extract was concentrated to give residue (12.0 g).

Example-10

Synthesis of Compound-Y

A mixture of compound-X (12.0 g), 3-Amino-2,2-dimethyl-propionitrile (4.2 g), 3.7 g 2-hydroxypyridine in 12 ml triethylamine was stirred for about 36 hours at 60-65° C. The progress of the reaction was monitored by HPLC analysis. After completion of the reaction it was concentrated to residue and the residue was dissolved in diisopropyl ether and stirred with aqueous NaOH to remove unreacted compound X. The layers were separated and the diisopropyl ether extract was concentrated to give residue (12.5 g).

Example-11

Synthesis of Compound-Z

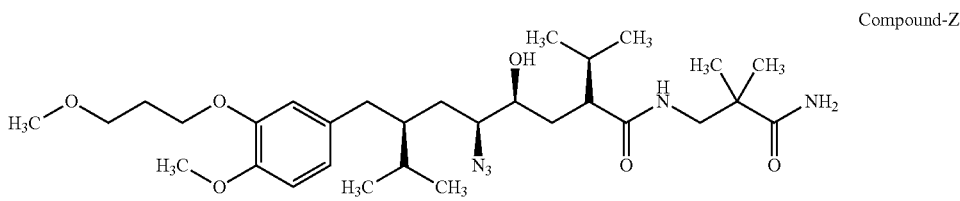
Compound-Z

To a solution of Compound-Y (13 g, obtained in example 2) was dissolved in aqueous NaOH (5 g dissolved in 45 ml of DM water), 35% Hydrogen peroxide (20 ml) was added at room temperature and stirred the at 30°-40° C. for 2-4 h. The progress of the reaction was monitored by HPLC analysis. After completion of the reaction the peroxides were destroyed by stirring with sodium bisulfite solution. Thereafter product was extracted in dichloromethane (3×75 ml). The dichloromethane extract was washed with brine and concentrated to obtain compound Z as a viscous liquid (12.3 g).

Example-12

Synthesis of Aliskiren Hemifumarate

Compound-Z (12.3 g, obtained in example 3) and of ethanolamine (1.3 g) were dissolved in ethanol and hydrogenated at about 3 Kg pressure in presence of Pd/C (600 mg, 5% w/w) for 3-4 h. The catalyst was filtered and the clear filtrate was treated with fumaric acid (1.23 g). The solution was filtered through Celite pad to get a particle free solution which was further concentrated under reduced pressure below 40° C. Acetonitrile was added to the concentrate and distillation was continued to remove residual ethanol. To this residue a mixture of acetonitrile/ethanol (97:3) was added and the obtained solution was stirred overnight to crystallize the product. The product slurry was cooled, filtered and washed with pre chilled acetonitrile. The product was dried under vacuum at 35° C. to give the Aliskiren hemifumarate (9 g).

Example-13

Synthesis of Aliskiren Hemifumarate

Compound-Z (6 g) and ethanolamine (0.9 g) were dissolved in methanol and hydrogenated at about 3 Kg pressure in presence of Pd/C (600 mg, 5% w/w) for 3-4 h. The catalyst was filtered and the clear filtrate was treated with fumaric acid (600 mg). The solution was filtered through Celite pad to get a particle free solution which was further concentrated under reduced pressure below 40° C. Acetonitrile was added to the concentrate and distillation was continued to remove residual methanol. To this residue a mixture of acetonitrile/ethanol (97:3) was added and the obtained solution was stirred overnight to crystallize the product. The product slurry was cooled, filtered and washed with pre chilled acetonitrile. The product was dried under vacuum at 35° C. to give the Aliskiren hemifumarate (4 g).

Example-14

Process for the Preparation of Aliskiren Hemifumarate from Compound of Formula-IV (where $R_1=OCH_2OCH_2CH_3$, $R2=OCH_3$, $R_3$, $R_4=-CH(CH_3)_2$)

The azide compound of Formula-IV was hydrogenated for 4 hours in the presence of 10% Pd/C (1 g) and ethanolamine (1 g) in ethanol (100 ml) at ambient temperature and 3.0 Mbar pressure. The reaction mixture was filtered and the catalyst was washed with ethanol (25 ml). The obtained residue was dissolved in tert-butyl methyl ether and consequently washed with water and brine. The combined organic phases were dried over anhydrous sodium sulfate and concentrated to give the residue. The residue was mixed with fumaric acid (0.5 g) dissolved in ethanol and filtered. The filtrate was concentrated by evaporation to a total weight of 7.0 grams and dissolved in acetonitrile (125 ml) at 35° C. The resulting mixture was inoculated with 10 mg of Aliskiren hemifumarate and agitated for 17 hours at ambient temperature. The suspension was cooled to 0° C. and filtered off by suction after 2 hours. The residue was washed with acetonitrile and then dried under vacuum at 35° C. to yield Aliskiren hemifumarate as white crystals.

Example-15

Process for the Preparation of Aliskiren Hemifumarate from Compound of Formula-IV (where $R_1=OCH_2OCH_2CH_3$, $R2=OCH_3$, $R_3$, $R_4=-CH(CH_3)_2$)

The azide compound of Formula-IV was hydrogenated for 4 hours in the presence of 10% Pd/C (1 g) and ethanolamine (1 g) in methanol (100 ml) at ambient temperature and 3.0 Mbar pressure. The reaction mixture was filtered and the catalyst was washed with methanol (25 ml). The obtained residue was dissolved in tert-butyl methyl ether and consequently washed with water and brine. The combined organic phases were dried over anhydrous sodium sulfate and concentrated to give the residue. The residue was mixed with fumaric acid (0.5 g) dissolved in ethanol and filtered. The filtrate was concentrated by evaporation to a total weight of 7.0 grams and dissolved in acetonitrile (125 ml) at 35° C. The resulting mixture was inoculated with 10 mg of Aliskiren hemifumarate and agitated for 17 hours at ambient temperature. The suspension was cooled to 0° C. and filtered off by suction after 2 hours. The residue was washed with acetonitrile and then dried under vacuum at 35° C. to yield Aliskiren hemifumarate as white crystals.

We claim:
1. A process for the preparation of Aliskiren or a pharmaceutically acceptable salt thereof comprising the steps of:
   a) converting the cyano group of a compound of Formula-III into an amide group to give a compound of Formula-IV;

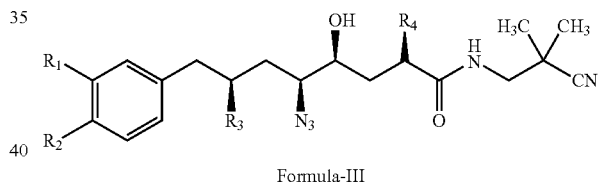

Formula-III

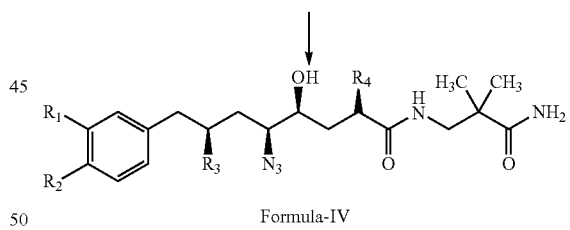

Formula-IV wherein $R_1$ is $O(CH_2)_3OCH_3$, $R_2$ is OMe; and $R_3$ and $R_4$ are $CH(CH_3)_2$;
   b) reducing the azide group of the compound of Formula-IV to form an amine group and isolating the resulting compound of Formula-Ia; and

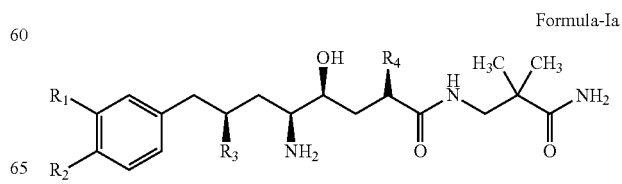

Formula-Ia c) optionally converting the compound of Formula-Ia into a pharmaceutically acceptable salt.

2. The process according to claim 1, wherein the compound of Formula-III is prepared by reacting the compound of Formula-II with 3-amino-2,2-dimethyl-propionitrile

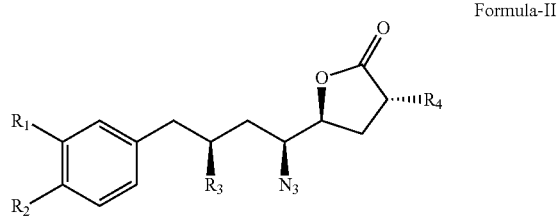
Formula-II wherein $R_1$ is $O(CH_2)_3OCH_3$; $R_2$ is OMe; and $R_3$ and $R_4$ are $CH(CH_3)_2$.

3. The process according to claim 1, wherein the reduction of the azide group of the compound of Formula-IV is carried out by using a palladium catalyst.

4. The process according to claim 1, wherein the reduction of the azide group of the compound of Formula-IV is carried out in the presence of an alcoholic solvent.

5. The process according to claim 4, wherein the alcoholic solvent used in the reduction of the azide compound of Formula-IV is selected from the group consisting of ethanol, methanol, and isopropanol.

6. The process according to claim 2, wherein the compound of Formula-II is prepared from a compound of Formula-V by cyclisation and azidation,

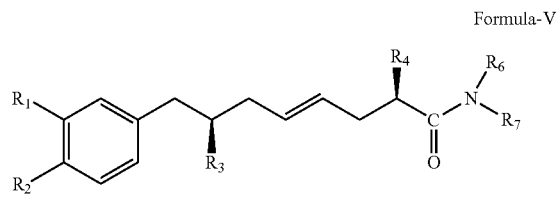
Formula-V wherein $R_1$ is $O(CH_2)_3OCH_3$; $R_2$ is OMe; $R_3$ and $R_4$ are $CH(CH_3)_2$; R6 is C1-C6 alkyl; and R7 is C1-C6 alkyl or C1-C6 alkoxy.

7. The process according to claim 6, wherein the compound of Formula-V is purified by fractional distillation.

8. A compound of Formula-III

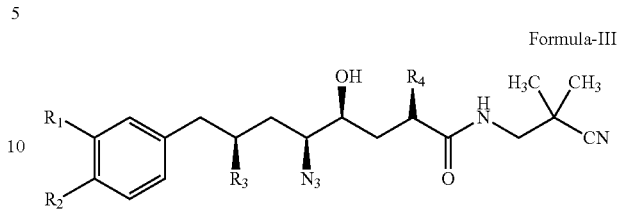
Formula-III wherein $R_1$ is $O(CH_2)_3OCH_3$; $R_2$ is OMe; and $R_3$ and $R_4$ are $CH(CH_3)_2$.

9. In a multi-step process for the production of Aliskiren or a pharmaceutically acceptable salt thereof in which a compound of Formula-III is a starting compound

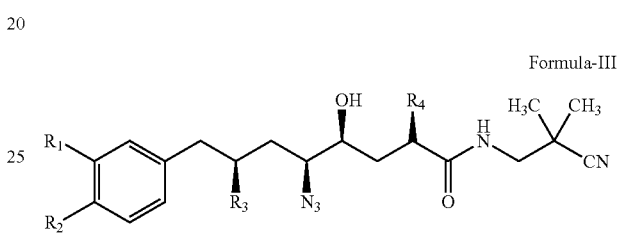
Formula-III wherein $R_1$ is $O(CH_2)_3OCH_3$; $R_2$ is OMe; and $R_3$ and $R_4$ are $CH(CH_3)_2$ the process comprising the conversion of the cyano group into an amide group and the reduction of the azide group to form an amine group.

10. A compound of Formula-A1

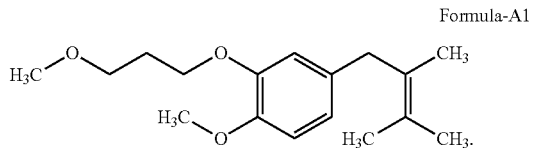 [SMILES: COCCCOc1cc(CC(C)=C(C)C)ccc1OC]
Formula-A1

* * * * *